United States Patent [19]

Gruber et al.

[11] Patent Number: 5,062,891

[45] Date of Patent: Nov. 5, 1991

[54] METALLIC INKS FOR CO-SINTERING PROCESS

[75] Inventors: William C. Gruber, Arlington; Eric A. Barringer, Waltham, both of Mass.

[73] Assignee: Ceramics Process Systems Corporation, Milford, Mass.

[21] Appl. No.: 85,077

[22] Filed: Aug. 13, 1987

[51] Int. Cl.$^5$ .............................. C09D 11/00

[52] U.S. Cl. ................................ 106/20; 106/1.13; 106/1.14; 106/1.15; 106/403; 106/483; 252/514

[58] Field of Search .................... 106/20, 308 Q, 1.13, 106/1.14, 1.15, 403, 483; 252/514

[56] References Cited

U.S. PATENT DOCUMENTS

| | | | |
|---|---|---|---|
| 4,090,009 | 5/1978 | Horowitz | 106/1.19 |
| 4,172,919 | 10/1979 | Mitchell | 106/1.13 |
| 4,514,321 | 4/1985 | Siuta | 106/1.12 |
| 4,521,329 | 6/1985 | Siuta et al. | 106/1.14 |
| 4,551,357 | 11/1985 | Takeuchi | 427/96 |

FOREIGN PATENT DOCUMENTS 1129560 8/1982 Canada.

OTHER PUBLICATIONS

Derwent, Abstract Accession No. 87-160917/23, Japanese Pat. No. 62096377, May 2, 1987.

*Primary Examiner*—Amelia Burgess Yarbrough

[57] ABSTRACT

Metallization, applied by the thick film screening technique, utilized herein has glass-ceramic bonding agents designed to promote adhesion yet maintain the desired electrical properties and post-processing characteristics.

31 Claims, No Drawings

METALLIC INKS FOR CO-SINTERING PROCESS

BACKGROUND

1. Field of Invention

This invention relates to glass-ceramic composite packages for integrated circuits in general, and in particular to metal conductive compositions used for circuit traces and vias to form the interconnective thick film wiring.

2. Description of Prior Art

Multi-layer ceramic substrates for mounting integrated circuit chips generally comprise alternating layers of metallic circuits and ceramic insulating layers to form three dimensional interconnect circuits. The substrates are produced either by a thick film printing method or a green sheet lamination method.

The thick film printing method has been used to fabricate hybrid circuits and multi-layer printed interconnect boards. In this process, metal powders and ceramic powders are formulated into metal and dielectric (insulator) inks and then alternately screen printed onto a fired ceramic base. Generally two or three printings of dielectric material are required for every insulating layer and the circuit must be fired after each printing process. Thus, this method is very time consuming because of the large number of printing and firing steps required. The method is also prone to low production yields and is limited in the density of interconnect circuitry. Ceramic layer hermeticity is a major problem affecting yields and is a direct result of using screen printing methods to form insulating layers. In addition, conventional metal pastes contain active bonding agents to promote adhesion to ceramic substrates (e.g., lead borosilicate glass and bismuth oxide) which function acceptably in air fired applications, but which are problematic in nitrogen firing applications.

According to the green sheet lamination method, green ceramic sheets on which metal circuits have been printed are successively laminated and then co-fired to form a monolithic interconnect structure (package). Generally, the ceramic green tape is fabricated by the doctor blade casting process from a slurry containing a mixture of ceramic powders, thermoplastic resin, solvents, and other additives (dispersants, plasticizer). Polyvinyl butyral (PVB) is the most commonly used resin system for tape formation. The green tape is blanked into sheets and registration holes are punched. Via holes, which in the final package serve as vertical interconnects between layers, are punched using fixed tooling or a numerically controlled punch press. The via holes are filled and circuit trace patterns are printed using the desired metallization compositions. The individual sheets are then stacked in the proper sequence and laminated to form a solid, composite laminate. The laminate is fired to decompose and remove the organic binder and to sinter the ceramic and metal particles, thus forming a dense body containing the desired three-dimensional wiring pattern.

Aluminum oxide, because of its excellent electrical (insulating), thermal, and mechanical (especially strength) properties has been the ceramic of choice for such substrates. These ceramic bodies, generally containing 4–10 weight percent glass, require sintering temperatures above 1500° C., which thus necessitates the use of refractory metals such as molybdenum or tungsten for the wiring. These metals have poor electrical conductivity as compared to highly conductive metals such as copper, and secondly, they require the use of strongly reducing atmospheres during co-firing necessitating expensive furnace systems. Alumina has been an adequate dielectric material for microelectronic packaging in the past; however, the advent of higher frequency and higher speed devices has made clear the deficiencies of the current materials systems. $Al_2O_3$ has a relatively high dielectric constant of about 9.8, causing high signal propagation delay and low signal-to-noise ratio (crosstalk). Furthermore, alumina has a thermal expansion of $6.7 \times 10^{-6}/°$ C. (20–200°) C. range) as compared to about $3.0-3.5 \times 10^{-6}/°$ C. for silicon, which represents significant mismatch in thermal expansion and results in design constraints and reliability concerns (e.g., flip chip technology). Furthermore, the binders used to fabricate green tape do not decompose cleanly during firing at low temperatures (200–600° C.) in reducing atmospheres utilized; significant graphitic carbon is generated which requires a high temperature burnout treatment (1100–1200° C.) prior to raising the temperature to the peak firing condition.

Accordingly, there exists a need for a materials system which allows co-sintering of the ceramic with a conductive metal such as copper, gold, or silver. An IC package fabricated from this system would have significantly improved signal transmission characteristics. To this end, a glass-ceramic material sinterable to a high density at temperatures less than 1000° C. is desirable. To allow co-sintering with copper in a non-oxidizing atmosphere, in particular, the binder material must depolymerize and burnout cleanly, which precludes the use of conventional binders such as PVB. PVB or similar polymers would result in a porous ceramic and carbonaceous residue, thereby deteriorating the mechanical strength and electrical insulation. There also exists a need for a metallurgical system that yields good conductivity, adhesion and solderability when co-fired with the ceramic dielectrics. Furthermore, for optimum yields and performance, the bonding agents and ink vehicle system should be compatible with gold, silver/palladium alloys, and copper.

Extensive prior art exists in the area of metallic inks for thick-film conductors; prior art in copper containing inks is especially relevant to the present case, although significant portions of the following discussion apply to air-fired metallization (Ag, Ag/Pd, Au) as well. Examples of prior art include: Suita, U.S. Pat. No. 4,540,604 (9/85); Mitchell, U.S. Pat. No. 4,172,919 (10/79); Hoffman, U.S. Pat. No. 4,070,518 (1/78); and Grier, 4,072,771 (2/78). Suita contains an excellent review of prior part in copper metallization, and is therefore hereby incorporated herein by reference.

Thick film conductor patterns are typically formed on green tape by screen printing of metallic inks; these inks generally comprise a metal powder, glassy bonding agent powders, other solid additives, and a vehicle system (solvents, dispersant, binder (s), and other organics). The ratio of these components determines the rheology and printing characteristics of the ink. Inks typically contain approximately 70–92 weight percent solids with the balance being the vehicle system. Commercially available inks typically employ metal powders and powdered bonding agents having average particle size between about 0.5–5 micrometers. Typical vehicle components are: ethyl cellulose or methacrylates (as binders) and slow drying solvents such as terpeniol, butyl carbitol acetate and butyl carbitol.

A common bonding agent used in the art is lead borosilicate glass containing approximately 45-65% PbO. Bismuth oxide ($Bi_2O_3$) is often added to promote glass wetting of the metal, and hence adhesion. Alkali metal oxides ($Na_2O$, $K_2O$) are also often added to the glass to reduce the viscosity of the glass during firing. Copper-based inks may also contain additional components such as copper oxide (1-4%) to improve adhesion of copper to the ceramic. In addition, the use of refractory metals to aid in copper oxide reduction to copper during firing, and thus to improve subsequent solder wetting, has been disclosed (e.g., see Suita).

Present inks, which were designed primarily for thick film hybrids and multilayer boards, are suboptimal for use in low temperature co-firing processes, especially when nonoxidizing atmospheres are required. While $Bi_2O_3$ has been found useful in air fired applications to assist in bonding, it has been found undesirable when used with nitrogen atmospheres, both in co-firing and in post-firing techniques. Bismuth oxide is reduced in such atmospheres to metallic bismuth which causes embrittlement of copper metallization. Alkali ions are potentially harmful in that they not only increase fluidity of the glass during firing, they also enhance migration of copper (in nonoxidizing atmospheres) and silver (in air) ions into the glass through ion exchange processes. As excessive metal migration may degrade electrical properties of the fired ceramic-metal body (package), the concentration of alkali ions should be minimized. In addition, alkali ions may leach out of the glassy bond phase during exposure to moisture and degrade the environmental stability of the package. Finally, copper oxide has been used to enhance adhesion of the metal trace to ceramics, especially alumina; however, bonding mechanisms involving copper oxide reactions may not be operative in the present case. Accordingly, there is a need for an improved metal ink system, which is co-firable at temperatures approximately less than 1000° C. with glass-ceramic substrates.

DISCLOSURE OF THE INVENTION

We have succeeded in the design and fabrication of metal ink compositions for use as thick-film conductors and co-firable with glass-ceramic composite substrates at temperatures of approximately less than 1000° C. The inks, comprising metal powders, glass-ceramic bond promoting additives and a vehicle, provide a fired metal conductor which meets all the physical and electrical requirements of microelectronic applications. Although the following description is focussed on copper inks, much of the discussion applies to many air-fired metal inks.

DESCRIPTION OF THE SPECIFIC EMBODIMENTS

Conductor patterns are typically formed on green tape by screen printing metallic inks. Metallic inks are typically made up of a powdered metal, powdered bonding agents and a vehicle system (solvent(s), binder(s), and dispersant). The ratio of these constituents and other desired additives determines the rheology and printing characteristics of the inks. They tend to range from approximately 70-92% solids by weight with the rest being the vehicle system. Low temperature co-firing and especially firing in a reducing atmosphere makes present inks suboptimal for use in the present invention.

Commercially available copper inks generally employ metals with particle sizes between approximately 0.5 and 5 micrometers. In a preferred embodiment of this invention, the copper is a relatively uniform and non-agglomerated powder whose average size ranges from approximately 1-10 micrometers. It is preferred that the powder have a relatively narrow size range, but the invention is not limited to narrow size range powders and is equally applicable to those having conventional sizes. A further embodiment, however, uses a blend of discrete sized particle populations to control the shrinkage during firing.

The ceramic-metal bond-promoting agents of the present invention generally comprise a calcium magnesium borosilicate (CMBS) glass plus either cordierite, forsterite, alumina, quartz, or other low thermal expansion silicates, for example, eucryptite or spodumene, or a combination of these. We have found that it is desirable to use some of the same constituents in both the trace and via inks as are found in the substrate, albeit in differing amounts and proportions. This provides for more uniform shrinkage of the entire piece during firing. Further, it has been found that as one increases the percentage of cordierite, or other low thermal expansion silicates, the thermal expansion coefficient of the fired metallization decreases. This finding is critical for via ink compositions for which minimal thermal expansion mismatch between the metallization and the glass ceramic substrate is desired.

The preferred solids content of the inks of the present invention are as follows. For trace inks approximately 80-97 volume percent metal is preferred, with the balance being 3-20 volume percent additives for bond promotion or other desired properties. More preferred trace formulations contain approximately 85-94 volume percent copper, 1-3 volume percent alumina, 2-8 volume percent cordierite or quartz, and 3-12 volume percent CMBS glass. For via inks, the metal should preferably range from approximately 40-70 volume percent, and the remaining 30-60 volume percent containing desired additives. More preferred via formulations contain approximately 50-70 volume percent copper, 2-10 volume percent alumina or quartz, 10-35 volume percent cordierite or low thermal expansion silicate and 10-40 volume percent CMBS glass.

The glass should be compatable with the substrate. Preferred glass compositions contain 25-57% (by weight) alkaline earth oxides (MO), 23-35% $SiO_2$, 25-35% $B_2O_3$ and 0-10% $Al_2O_3$, where the preferred percentage of alkaline earth oxide (MO) present as MgO is 0-50% and the balance thereof is CaO.

Preferred inks of the present invention contain approximately 75-92% by weight of solids, the remainder being the vehicle. The vehicle system is generally comprised of solvent(s), polymeric binder, and dispersant; a plasticizer and other additives may be present to modify the properties of the ink or printed patterns. Although useful solvents for inks generally include aliphatic alcohols, acetates, proprionates and terpenes, the preferred solvent for copper inks is alpha-terpineol. Butyl carbitol or butyl carbitol acetate may be used with terpineol for silver, silver/palladium, or gold inks to minimize the viscosity; however, such solvents are not recommended for copper inks used in co-firing applications.

The preferred polymers for inks of the present invention are polymethylmethacrylates of the lower alcohols, with butyl methacrylate being the most preferred. An example of a preferred polymer is Elvacite-2046 brand n-butylmethacrylate/isobutyl methacrylate obtained from E.I. DuPont de Nemours Corp., Wilmington, DE. Plasticizers, such as phthlatates, may be added to the vehicle to modify the properties of the binder. Preferred plasticizers include dibutyl phthlate and PX-316 (mixed phthlate obtained from USS Chemicals, Pittsburgh, PA). The preferred vehicle compositions range from about 15-35 weight percent binder and 65-85% solvent. Dispersants, at a concentration of 0.5-2 weight percent of the solids portion, may be added to the ink to improve the viscosity and printing characteristics of the inks. Preferred dispersants include, but are not limited to, Emcol CC-42, Emcol CC-36, Emcol CC-55, (the foregoing obtained from Witco Chemical Co., Perth Amboy, NJ) Triton X-100 (Rohm & Haas, Philadelphia, PA) and Span-85 (ICI Americas, Inc., Wilmington, DE).

The firing temperature of the copper inks is generally between 700 and 950° C. Although pure copper sinters at the lower temperatures (about 650-800° C.), the co-firing of copper with the glass-ceramic dielectric (more thoroughly discussed in co-pending U.S. applications Ser. Nos. 085,078 (now U.S. Pat. No. 4,788,046) and 085,950, both filed contemporaneously herewith, which are hereby incorporated herein by reference) is generally accomplished between 875-950° C. Thus one objective of the present invention is to delay the sintering of copper to thus minimize the mismatch in shrinkage behavior between the copper and the glass-ceramic.

Glass-ceramic additions to the ink, where these constituents comprise some of the components of the glass-ceramic, are effective in significantly delaying the sintering process and thereby improving the shrinkage match. However, additional retardation may be desirable and can be effected by the addition of copper oxide (less than about 5%) to the ink. Although the prior art discloses the addition of copper oxides to the inks, such additions are made to enhance the copper-to-ceramic adherence, whereas in the present invention copper oxide may be employed to retard sintering of the copper. Copper oxide may be added as a powder, or, preferably achieved through the oxidation treatment (200-500° C. in air) of the copper powder. An alternate approach is to co-fire at elevated oxygen levels (for example 30-100 ppm $O_2$) and thus partially oxidize the copper prior to reaching sintering temperatures (less than approximately 650°). In either case, the copper oxide may be reduced by the introduction of hydrogen into the atmosphere at a desired temperature; sintering of the copper accelerates once the copper oxide is adequately reduced. Thus, a preferred embodiment of the present invention is the use of copper oxide to delay sintering of the copper, thereby providing for improved shrinkage match between the copper and the ceramic dielectric.

Inks made in accordance with the present invention showed good printing characteristics and, upon sintering, adhered well to the ceramics. Typical resistivities for trace inks were approximately 1-2 milliohm/square, and for via inks were approximately 3-8 milliohm/square.

The present invention may be more readily appreciated by reference to the following examples:

EXAMPLE 1

The following table shows typical solids formulations for inks used in vias and traces, and made in accordance with the present invention. Amounts shown are given in volume percent.

|       | Copper | Alumina | Cordierite | Quartz | CMBS glass |
|-------|--------|---------|------------|--------|------------|
| via   | 60     | 5       | 10         | 0      | 25         |
| via   | 60     | 7       | 8          | 5      | 20         |
| trace | 85     | 2       | 4          | 0      | 9          |
| trace | 85     | 2       | 4          | 2      | 7          |

Inks made with the above formulation had a total solids content of 85-91 wt%, and the vehicle comprised 9-15 wt%. Composition of the CMBS glass was 33.0% $SiO_2$, 31.0% $B_2O_3$, 6.75% MgO, 20.25% CaO and 9.0% $Al_2O_3$.

EXAMPLE 2

The solids formulations of Example 1 were mixed with a "vehicle" containing 25 wt% E-2046 brand and 75 wt% alpha terpineol, and a dispersant (Emcol CC-36 at 1 wt%). If desired, a phthalate plasticizer (at 15-30% of the weight of the polymeric binder) may also be added.

The total weight of the vehicle system was from 9-12% of the total weight of all ingredients. The volume of the organics made up 48-57% of the total volume of the paste.

If viscosity of the paste needed to be adjusted, extra alpha terpineol (5-15% of the original weight) or extra vehicle was added.

EXAMPLE 3

The following illustrates the effect of copper oxide on sintering rates. Copper pellets were made by pressing copper #12 powder (obtained from Metz Metallurgical, South Plainfield, NJ) to a green density of 64%. Samples were subjected to the following oxidation treatment:

| temperature | time  | wt % increase |
|-------------|-------|---------------|
| 200°        | 6 hrs | 0.2 wt %      |
| 300°        | 6 hrs | 3.1           |
| 400°        | 6 hrs | 6             |

X-ray analysis showed that the weight gain was primarily due to the presence of $Cu_2O$.

Oxidized and non-oxidized pellets were sintered in a $N_2$ atmosphere. Temperature was raised to peak temperatures of 900° and 1000° at the rate of 20°/min. Densities are given below:

|              | 900°    | 1000°   |
|--------------|---------|---------|
| oxidized     | 65-75%  | 80-85%  |
| non-oxidized | 90-91%  | 95+ %   |

Samples which were oxidized prior to firing underwent a reduction reaction at their surface. This resulted in the formation of a copper "skin" surrounding the pellet of oxidized copper, whereas the internal region of the pellets showed poor sintering.

Additional pellets which were subjected to the 200° C. oxidation treatment described above were fired in nitrogen, but this firing profile included a 2-hour hold at 760° in the presence of forming gas (approximately 5% $H_2$), prior to reaching a peak temperature of 1000°. The pellets sintered to approximately 90% density. Pellets treated by oxidizing at 400° C. and fired as described reached 87% density. Thus, the reduction step resulted in improved sintering; however, it appears that excess $Cu_2O$ (more than about 5%) is difficult to adequately reduce and hence is detrimental to sintering.

Loose copper powder which was oxidized at 300° C. for 3 hours had a 14% weight gain, due primarily to the formation of $Cu_2O$. However, upon exposure to forming gas at 600°, the oxide was rapidly reduced, as evidenced by the powder returning to its original weight within 5 minutes. Thus, the ability to reduce copper oxides to copper in practice seems to be limited by gas diffusion into the body (pellets); this phenomenon would also apply generally to multi-layer copper cofired substrates.

We claim

1. A metallic ink consisting essentially of:
   (a) powdered metal particles selected from the group consisting of copper, silver, palladium, gold, alloys thereof, and mixtures thereof;
   (b) an organic vehicle system;
   (c) a glass component consisting essentially of: (i) 25-57 wt. % alkaline earth oxides, of which MgO comprises 0-50 wt. % and of which CaO comprises 50-100 wt. %; (ii) 23-35 wt. % $SiO_2$; (iii) 25-35 wt. % $B_2O_3$; and (iv) 0-10 wt. % $Al_2O_3$; and
   (d) at least one ceramic material selected from the group consisting of: cordierite, forsterite, alumina, quartz, eucryptite, and spodumene.

2. An ink according to claim 1, wherein the metal powder has a narrow size range of approximately 1-10 micrometers.

3. An ink according to claim 1, wherein the metal powder consists essentially of a mixture of discrete narrow size range populations and wherein each population has an average size range from between 1 micrometer and 10 micrometers.

4. An ink according to claim 1, wherein the metal particles, ceramic material, and glass are present in sufficient amounts to equal approximately 75-92 weight percent of the total ink.

5. An ink according to claim 4, wherein the metal particles are copper.

6. An ink according to claim 5, further comprising an amount of copper oxide effective to control the shrinkage of the copper metal particles during sintering.

7. An ink according to claim 6, wherein the copper oxide is present in an amount less than about 5 weight percent.

8. A metallic ink comprising a solids portion comprising:
   (i) powdered metal particles selected from the group consisting of copper, silver, palladium, gold, alloys thereof, and mixtures thereof;
   (ii) glass consisting essentially of
      (a) 25-57 wt. % alkaline earth oxides, of which MgO comprises 0-50% and CaO comprises 50-100%,
      (b) $SiO_2$: 23-35%
      (c) $B_2O_3$: 25-35%
      (d) $Al_2O_3$: 0-10%;
   (iii) at least one ceramic material selected from the group consisting of cordierite, forsterite, alumina, quartz, eucryptite, and spodumene; the solids being dispersed in an organic vehicle system including a solvent and a polymeric binder.

9. An ink according to claim 8, wherein the solvent is selected from the group consisting of aliphatic alcohols, acetates, propionates, terpenes, alpha-terpineol, butyl arbitol, and butyl carbitol acetate.

10. An ink according to claim 9, wherein the polymeric binder is a polymethylmethacrylate of a lower alcohol.

11. An ink according to claim 10, wherein the polymeric binder is butyl methacrylate.

12. An ink according to claim 10, wherein the vehicle system further comprise a plasticizer.

13. An ink according to claim 12, wherein the plasticizer comprises phthalates.

14. An ink according to claim 13, wherein the phthalates are a mixture of phthalates.

15. An ink according to claim 10, wherein the vehicle system further comprises a dispersant.

16. An ink according to claim 15, wherein the dispersant is selected from the group consisting of: a polypropoxy quaternary ammonium chloride; a polypropoxy quaternary ammonium acetate; sorbitan trioleate; octylphenoxy polyethoxy ethanol; and mixtures thereof.

17. An ink according to claim 15 wherein the dispersant is present in an amount equal to approximately 0.5-2 weight percent of the solids portion.

18. A metallic ink comprising a solids portion comprising (i) approximately 50-70 volume percent copper powder; (ii) approximately 10-40 volume percent CMBS glass, the glass consisting essentially of:
   (a) 25-57 wt. % alkaline earth oxides of which MgO comprises 0-50% and CaO comprises 50-100%;
   (b) $SiO_2$: 23-35%
   (c) $B_2O_3$: 25-35%
   (d) $Al_2O_3$: 0-10%;
   (iii) approximately 2-10 volume percent alumina or quartz; and (iv) 10-35 volume percent of at least one ceramic material selected from the group consisting of cordierite, forsterite, eucryptite, and spodumene; and solids being dispersed in an organic vehicle system comprising a solvent and a polymeric binder.

19. An ink according to claim 18, the ink comprising approximately 60 volume percent copper, 5 volume percent alumina, 10 volume percent cordierite, and 25 volume percent CMBS glass.

20. An ink according to claim 18, the ink comprising approximately 60 volume percent copper, 7 volume percent alumina, 8 volume percent cordierite, 5 volume percent quartz and 20 volume percent CMBS glass.

21. An ink according to claim 18, further comprising a shrinkage controlling agent.

22. An ink according to claim 21, wherein the shrinkage controlling agent is copper oxide.

23. An ink according to claim 26, wherein the copper oxide is present in the form of copper oxide powder and in an amount of less than approximately 5 wt. %.

24. An ink according to claim 23, wherein the copper oxide is present in the form of copper oxide coated copper particles.

25. An ink comprising a solids portion comprising (i) approximately 85-94 volume percent copper; (ii) 1-3 volume percent alumina; (iii) 3-12 volume percent CMBS glass, the glass consisting essentially of:
   (a) alkaline earth oxides, 25-57 wt.%, of which MgO comprises 0-50% and CaO comprises 50-100%,
   (b) $SiO_2$: 23-35%
   (c) $B_2O_3$: 25-35%
   (d) $Al_2O_3$: 0-10%;

and (iv) 2–8 volume percent cordierite or quartz, the solids being dispersed in an organic vehicle system comprising a solvent and a polymeric binder; the ink suitable for use in traces.

26. An ink according to claim 25, the ink comprising approximately 85 volume percent copper, 2 volume percent alumina, 4 volume percent cordierite and 9 volume percent CMBS glass.

27. An ink according to claim 25, the ink comprising approximately 85 volume percent copper, 2 volume percent alumina, 4 volume percent cordierite, 2 volume percent quartz and 7 volume percent CMBS glass.

28. An ink according to claim 25, further comprising a shrinkage controlling agent.

29. An ink according to claim 28, wherein the shrinkage controlling agent is copper oxide.

30. An ink according to claim 29, wherein the copper oxide is present in the form of copper oxide powder, and in an amount of less than approximately 5 wt%.

31. An ink according to claim 30, wherein the copper oxide is present in the form of copper oxide coated copper particles.

* * * * *